United States Patent [19]

Lange et al.

[11] Patent Number: 4,537,901
[45] Date of Patent: Aug. 27, 1985

[54] INSECTICIDAL CARBAMATES

[75] Inventors: Arno Lange, Bad Durkheim; Franz Merger, Frankenthal; Peter Hettinger, Edingen-Neckarhausen; Heinrich Adolphi, Limburgerhof, all of Fed. Rep. of Germany

[73] Assignee: BASF Aktiengesellschaft, Fed. Rep. of Germany

[21] Appl. No.: 620,564

[22] Filed: Jun. 14, 1984

[51] Int. Cl.³ .................. A01N 43/56; C07D 231/08; C07D 491/107
[52] U.S. Cl. .................. 514/404; 548/364; 548/365
[58] Field of Search .................. 548/364, 365; 424/273 P

[56] References Cited

U.S. PATENT DOCUMENTS 4,213,992 7/1980 Adolphi et al. .................. 424/273 P

FOREIGN PATENT DOCUMENTS 1580711 12/1980 United Kingdom ............ 424/273 P

Primary Examiner—Richard A. Schwartz
Assistant Examiner—Kurt G. Briscoe
Attorney, Agent, or Firm—Keil & Weinkauf

[57] ABSTRACT

Carbamates of the formula

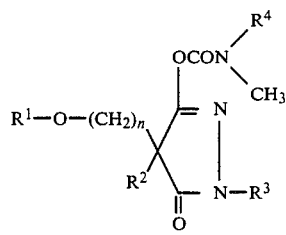

where either $R^1$ is straight-chain or branched alkyl of not more than 4 carbon atoms and $R^2$ is straight-chain or branched alkyl of not more than 6 carbon atoms, or $R^1$ and $R^2$, together with the molecular moiety which they include, form a 5-membered, 6-membered or 7-membered heterocyclic ring, $R^3$ is straight-chain or branched alkyl of not more than 6 carbon atoms or cycloalkyl of 3 to 6 carbon atoms, $R^4$ is methyl or methoxy, and n is 1 or 2, their preparation and their use as insecticides.

5 Claims, No Drawings

INSECTICIDAL CARBAMATES

The present invention relates to novel carbamates, a process for their preparation, and pesticides which contain these carbamates as active ingredients, as specifically claimed in the claims.

The carbamates of the invention are compounds of the formula

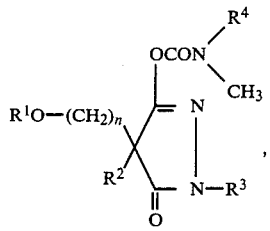

where either $R^1$ is straight-chain or branched alkyl of not more than 4 carbon atoms and $R^2$ is straight-chain or branched alkyl of not more than 6 carbon atoms, or $R^1$ and $R^2$, together with the molecular moiety which they include, form a 5-membered, 6-membered or 7-membered heterocyclic ring, $R^3$ is straight-chain or branched alkyl of not more than 6 carbon atoms or cycloalkyl of 3 to 6 carbon atoms, $R^4$ is methyl or methoxy, and n is 1 or 2.

$R^1$ can be, for example, methyl, ethyl, isopropyl or isobutyl.

In formula I, straight-chain or branched alkyl radicals $R^2$ are each, for example, methyl, ethyl, propyl, isopropyl or butyl. $R^1$ and $R^2$, together with the molecular moiety to which they are bonded, can form a ring, examples of preferred rings of this type being the tetrahydrofuran and the tetrahydropyran ring. Straight-chain or branched alkyl radicals $R^3$ are each methyl, ethyl, propyl or isopropyl, or one of the butyl, pentyl or hexyl radicals.

Depending on the substitution, the novel carbamates are yellowish or colorless oils or colorless solid substances which have a pronounced biological action, which enables them to be used as insecticides or acaricides for controlling animal pests. They have a particularly good action against sucking insects.

The novel carbamates can be obtained by reacting an appropriate salt of a pyrazolinone (II) with an appropriate carbamyl halide:

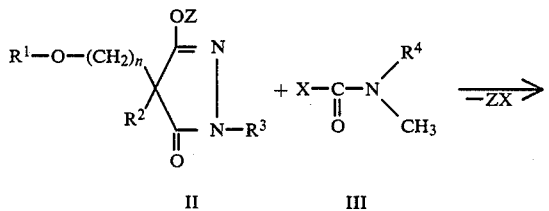

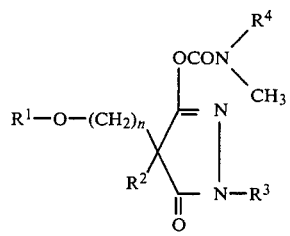

In these formulae, Z is a monvalent cation, preferably an alkali metal cation, or one equivalent of a polyvalent cation, and X is halogen, preferably chlorine or bromine.

The reaction can be carried out readily in a solvent or diluent. Examples of suitable solvents or diluents are ethers, such a diethyl ether, diisopropyl ether, tetrahydrofuran, dioxane or diglycoldimethyl ether, ketones, such as acetone, methyl ethyl ketone, diethyl ketone or diisopropyl ketone, aliphatic chlorohydrocarbons, such as dichloromethane, trichloromethane, carbon tetrachloride, 1,1-dichloroethane or 1,2-dichloroethane, aromatic hydrocarbons, such as toluene, xylenes or chlorobenzenes, dimethylformamide, nitromethane, and nitriles, such as acetonitrile or propionitrile.

In carrying out the process, the starting materials are generally employed in stoichiometric amounts. The reaction is promoted by an excess of up to 200% of the carbamyl halide, which is generally fairly cheaply available.

The reaction temperature can be varied within a relatively wide range. In general the reaction is carried out at no higher than 100° C., preferably from 30° to 90° C., and the boiling point of the diluent may constitute an upper limit for the temperature. A crown ether can be added as a catalyst.

The (hydroxy)pyrazolinone salts used as starting compounds can also be referred to as pyrazolidinedione salts can be prepared by a conventional method (Helv. Chim. Acta. 36, (1953) 74 et seq.), by reacting an appropriate disubstituted dialkyl malonate (IV) with a monosubstituted hydrazine (V) in the presence of a suitable condensing agent, e.g. sodium methylate:

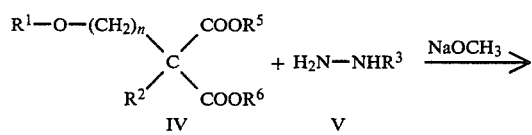

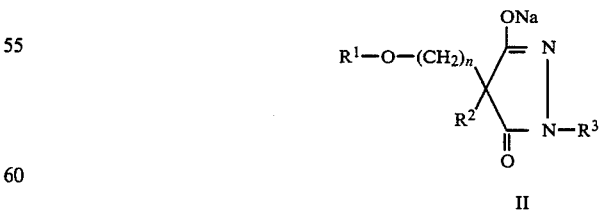

$R^5$ and $R^6$ are each preferably methyl or ethyl.

This process gives the salts of the pyrazolinones in good yield and purity. The salts can be isolated, for example, as follows: when the addition of the methylate is complete, the methanol formed is distilled off together with solvent (e.g. toluene, xylene, cumene, chlorobenzene or cyclohexane), until pure solvent passes over. The resulting crystalline salt is separated off from the solvent and is dried. The salt, in particular the sodium salt, can be used without further purification.

The malonate IV required for the preparation of the pyrazolinone salts can be prepared from the free acid by a conventional method (Weygand-Hilgetag, Org. Chem. Experimentierkunst 1970, 4th edition, pages 380–384). The free acids can be obtained from 2-alkyl-malonic acids and chloromethyl alkyl ethers, for example by a method given in Ar. 297 (4) (1964), 219 et seq.

However, the preparation of certain free 2-alkylmalonic acids from chloromethyl ethers does not constitute the most advantageous method, especially since chloromethyl ethers are deemed to be carcinogenic and are known to be dangerous.

It is therefore proposed to prepare the particularly important malonate IV, in which n is 1, starting from a 2-alkylacrolein V, formaldehyde and an n-alkanol. In the presence of a tertiary amine, these reactants first form a 2-hydroxymethyl aldehyde VI, which can be oxidized to the corresponding malonic acid VII, for example with nitric acid, and the product obtained can then be esterified.

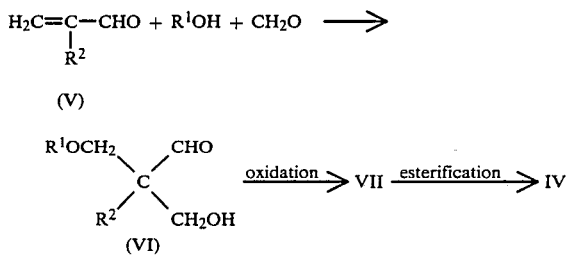

The conversion of V to VI is carried out at below 150° C., for example from 60° to 100° C., preferably in an aqueous medium, i.e. using aqueous formaldehyde under atmospheric pressure, a slight excess of formaldehyde and a greater excess of alcohol (e.g. from 4 to 6 moles per mole of acrolein) being advantageous. The oxidation and the esterification are conventional processes which have been described for similar substances.

EXAMPLE OF THE PREPARATION OF DIMETHYL ETHYLMETHOXYMETHYLMALONATE (a) Preparation of 2-methoxymethyl-2-hydroxymethylbutanal 41 g of triethylamine are added to a mixture of 1600 ml of methanol, 500 g of 30% strength formaldehyde solution and 328 g of 2-ethylacrolein in the course of 10 minutes, and the solution is then kept at 78° C. for 7 hours. Low-boiling components are distilled off, after which 390 g (67%, based on 2-ethylacrolein) of the title compound of boiling point 95°–100° C./3 mbar are isolated by distillation under reduced pressure.

(b) Preparation of methoxymethylethylmalonic acid 100 mg of $MnCl_2.H_2O$ are added to 400 ml of 66% strength nitric acid ($d^{20}=1.40$), after which 140 g of 2-methoxymethyl-2-hydroxymethylbutanal are added at 40° C. in the course of 45 minutes. The mixture is cooled to 0° C., and the precipitated acid is filtered off and dried.

Yield: 105 g, corresponding to 62%, based on the aldol

Melting point: 72°–75° C., decarboxylation taking place.

(c) Preparation of the malonate 225 g of anhydrous potassium carbonate and 144 g of ethylmethoxymethylmalonic acid in 500 ml of acetone are initially taken, 206 g of dimethylsulfate are added dropwise and the mixture is stirred under reflux for 5 hours. The mixture is cooled and then filtered under suction, the filtrate is evaporated down and the residue is taken up in chloroform. The solution is washed with water and aqueous sodium bicarbonate solution, dried and evaporated down, and the residue is distilled.

Yield: 141.3 g

Boiling point: 48°–57° C./0.1.

EXAMPLE OF THE PREPARATION OF METHYL TETRAHYDROPYRAN-3,3-DICARBOXYLATE 57.5 g of tetrahydropyran-3,3-dicarboxylic acid in 74 g of methanol are initially taken, and HCl gas is passed in at from 10° to 20° C., until the solution is saturated. Stirring is continued for 4 hours at room temperature, and 130 ml of toluene are added. The toluene phase is separated off, dried and evaporated down, and the residue is distilled.

Yield: 41.6 g

Boiling point: 85°–90° C./0.01.

EXAMPLE 1

2-Methyl-4-ethyl-4-methoxymethyl-5-dimethylcarbamyloxypyrazolin-3-one

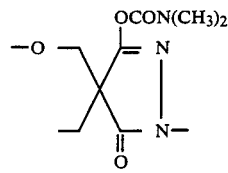

348 g of dimethyl ethylmethoxymethylmalonate are dissolved in 1.7 l of xylene, after which 87 g of methylhydrazine and 307 g of 30% strength sodium methylate solution are added dropwise. The methanol is then distilled off with simultaneous addition of xylene, until pure xylene passes over. The sodium salt of the pyrazolidinedione is filtered off under suction, washed with ether and dried, 317 g of product being obtained. 208 g of this product in 800 ml of acetone are initially taken, 0.1 g of 15-crown-5 is added, and 130 g of dimethylcarbamyl chloride are added dropwise, under reflux. Refluxing is continued for a further 3 hours, after which the mixture is cooled and then filtered under suction, and the filtrate is evaporated down. The crystals are filtered off under strong suction from the hot mixture and are washed with hexane. 147.1 g of a product of melting point 80°–83° C. are obtained.

Elemental analysis:

|  | C | H | N |
|---|---|---|---|
| Calculated: | 51.35% | 7.44% | 16.33% |
| Found: | 51.2% | 7.5% | 16.4% |

EXAMPLE 2

7-Oxa-2,3-diaza-2-methyl-spiro[4,5]dec-3-en-1-on-4-yl N,N-dimethylcarbamate

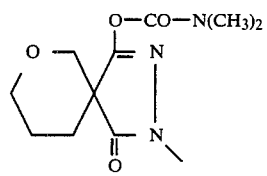

(a) Preparation of 3,3-bis-carboxytetrahydropyran 45 g of 3-formyl-3-hydroxymethyltetrahydropyran are added to a mixture of 600 g of nitric acid ($D^{20}=1.40$) and 0.1 g of $MnCl_2.H_2O$ at from 30° to 35° C. in the course of 90 minutes.

The excess nitric acid is then destroyed by adding a stoichiometric amount of formaldehyde solution.

The water is distilled off, after which the residue is taken up in a little diisopropyl ketone, and the product is crystallized out by cooling the solution. Yield: 58 g (40%, based on aldol); mp.: 140° C., with decarboxylation.

(b) 41.4 g of methyl tetrahydropyran-3,3-dicarboxylate are dissolved in 200 ml of xylene, and first 10.4 g of methylhydrazine and then 37.2 g of 30% strength sodium methylate solution are added dropwise. The bath temperature is then slowly increased to 170° C., and xylene is added dropwise at the rate at which methanol distils off. 50 of ether are added at room temperature, and the product is filtered off under suction, washed with ether and dried. 35.8 g of the sodium salt are obtained.

12.4 g of the sodium salt, 70 ml of acetone and 20 mg of 15-crown-5 are initially taken, 7.1 g of dimethylcarbamyl chloride are added dropwise, under reflux, and the mixture is kept at the boil for 4 hours. The acetone phase is filtered under suction, the filtrate is evaporated down and the residue is stirred thoroughly with hexane. 4.2 g of product of melting point 51°–53° C. are obtained.

Elemental analysis:

|  | C | H | N |
|---|---|---|---|
| Calculated: | 51.76 | 6.71 | 16.46 |
| Found: | 51.7 | 6.7 | 16.5 |

The compounds I below whose melting points are given or which are stated to be an oil were prepared by appropriately modifying the above examples. The remaining compounds can be obtained by modifying the preparation methods in an appropriate manner. On the basis of their structural similarity, they are expected to have an action similar to that of the compounds investigated in detail.

| No. | $R^1-O-(CH_2)_n-$ | $R^2$ | $R^3$ | $R^4$ | M.p. (°C.)/$n_D^{25}$ |
|---|---|---|---|---|---|
| 3 | $CH_3OCH_2-$ | $C_2H_5$ | $i-C_3H_7$ | $CH_3$ | 56–59 |
| 4 | $CH_3OCH_2-$ | $CH_3$ | $CH_3$ | $CH_3$ | 56–58 |
| 5 | $CH_3OCH_2-$ | $CH_3$ | $CH_3$ | $OCH_3$ | oil 1.476 |
| 6 | $CH_3OCH_2-$ | $CH_3$ | $i-C_3H_7$ | $CH_3$ | 41–44 |
| 7 | $-CH_2O-CH_2-CH_2-$ | | $CH_3$ | $CH_3$ | 51–53 |
| 8 | $CH_3OCH_2-$ | $n-C_3H_7$ | $CH_3$ | $CH_3$ | 62–65 |
| 9 | $CH_3OCH_2-$ | $n-C_3H_7$ | $C_2H_5$ | $CH_3$ | |
| 10 | $CH_3OCH_2-$ | $i-C_3H_7$ | $CH_3$ | $CH_3$ | 80–83 |
| 11 | $CH_3OCH_2-$ | $i-C_3H_7$ | $CH_3$ | $n-C_4H_9$ | |
| 12 | $CH_3OCH_2-$ | $n-C_4H_9$ | $CH_3$ | $CH_3$ | 39–42 |
| 13 | $CH_3OCH_2-$ | $n-C_4H_9$ | cyclo-$C_6H_{12}$ | $CH_3$ | |
| 14 | $C_2H_5OCH_2-$ | $n-C_3H_7$ | $CH_3$ | $CH_3$ | |
| 15 | $C_2H_5OCH_2-$ | $n-C_3H_7$ | $i-C_3H_7$ | $CH_3$ | |
| 16 | $C_2H_5OCH_2-$ | $i-C_3H_7$ | $CH_3$ | $CH_3$ | |
| 17 | $C_2H_5OCH_2-$ | $i-C_3H_7$ | $i-C_3H_7$ | $CH_3$ | |
| 18 | $C_2H_5OCH_2-$ | $i-C_3H_7$ | $i-C_3H_7$ | $CH_3$ | |
| 19 | $C_2H_5OCH_2-$ | $n-C_4H_9$ | $CH_3$ | $CH_3$ | |

The novel compounds are of particular interest because of their strong action on aphids. For this reasons, the agent selected for comparison purposes was Pirimicarb, a commercial product known to be an anti-aphid agent:

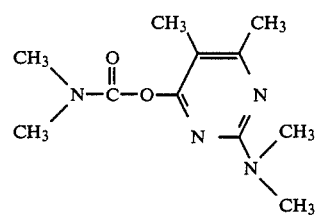

BIOLOGICAL EXAMPLE A

Continuous contact action on houseflies (Musca domestica)

The insides of Petri dishes 10 cm in diameter were lined with acetonic solutions of the active ingredients.

After the solvent had evaporated, 20 4-day old houseflies were introduced into each dish.

The kill rate was determined after 4 hours.

| Results: Compound no. | mg | Kill (%) |
|---|---|---|
| 1 | 0.02 | 100 |
| 3 | 0.01 | 80 |
| 4 | 0.01 | 100 |
| 6 | 0.02 | 100 |
| 7 | 0.2 | 100 |
| 8 | 0.2 | 100 |
| 10 | 0.2 | 100 |

BIOLOGICAL EXAMPLE B

Contact action on cotton stainers (Dysdercus intermedius)

Petri dishes 10 cm in diameter were lined with 1 ml of acetonic solutions of the active ingredients.

After the solvent had evaporated, 20 larvae of the penultimate stage were introduced into each dish and the action was registered after 24 hours.

| Results: Compound no. | mg | Kill (%) |
|---|---|---|
| 1 | 0.01 | 100 |
| 3 | 0.1 | 100 |
| 4 | 0.004 | 100 |
| 6 | 0.02 | 80 |
| 7 | 0.02 | 100 |
| 8 | 0.2 | 100 |
| Comparative | 0.2 | <50 |

-continued

| Results: Compound no. | mg | Kill (%) |
|---|---|---|
| agent | | |

BIOLOGICAL EXAMPLE C

Contact action on bean aphids (Aphis fabae); spray experiment

Potted bean plants (Vicia faba) with extensive aphid colonies were sprayed to runoff in a spray cabinet with aqueous formulations of the active ingredients. Assessment took place after 24 hours.

| Results: Compound no. | % | Kill (%) |
|---|---|---|
| 1 | 0.002 | 100 |
|  | 0.001 | approx. 90 |
| 4 | 0.0004 | 100 |
| 7 | 0.001 | 100 |
| Comparative | 0.002 | 100 |
| agent | 0.001 | <60 |

BIOLOGICAL EXAMPLE D

Systemic action on bean aphids (Aphis fabae); watering experiment

Bean plants growing in plastic pots (8 cm in diameter; 300 g of compost) and exhibiting heavy aphid attack were watered with 20 ml of aqueous formulations of the agents.

The kill rate was ascertained after 48 hours.

| Results: Compound no. | % | Kill (%) |
|---|---|---|
| 1 | 0.001 | approx. 90 |
| 3 | 0.04 | 100 |
| 4 | 0.01 | approx. 90 |
| 6 | 0.002 | 100 |

BIOLOGICAL EXAMPLE E

Persistence of effect of treated plants on aphids (Megoura viciae)

Young bean plants (Vicia faba) which had developed the first pair of true leaves were sprayed to runoff in a spray cabinet with aqueous formulations of the active ingredients. After the sprayed-on layer had dried the plants were infected with adult aphids. The action was determined after 24 hours.

If the kill rate was in the 80 to 100% range, the plants were against infected on the 2nd, 4th or 8th day, and the effects were observed.

| Results: Compound no. | % | Kill (%) after 4 days |
|---|---|---|
| 1 | 0.01 | 100 |
| 5 | 0.01 | 100 |
| Comparative agent | 0.01 | approx. 80 |

BIOLOGICAL EXAMPLE F

Persistence of action of systemic agents on aphids (Megoura viciae)

Young been plants in plastic pots (8 cm in diameter; 300 g of soil) were watered with 20 ml of aqueous active ingredient formulations. The plants were then infected with adult aphids. The action was monitored after 48 hours.

If the kill rate was above 80%, the plants were reinfected, and this was repeated after 4 to 8 days.

| Results: Compound no. | % | Kill (%) after 8 days |
|---|---|---|
| 1 | 0.01 | 100 |
| 5 | 0.01 | approx. 80 |
| Comparative agent | 0.01 | <60 |

BIOLOGICAL EXAMPLE G

Contact action on ticks (Ornithodorus moubata)

The experiment was carried out on young ticks which had sucked blood only once. Commercially available teabags, each containing 5 animals, were dipped for 5 seconds in the aqueous active ingredient formulation. The bags are then suspended. The temperature was kept at 25° to 26° C. The kill rate was determined after 48 hours.

| Compound no. | % | Kill (%) |
|---|---|---|
| 1 | 0.04 | 100 |
| 3 | 0.004 | 100 |
| 4 | 0.001 | 80 |
| 5 | 0.1 | 100 |
| 6 | 0.004 | 100 |
| 7 | 0.1 | 100 |
| 8 | 0.04 | 100 |
| Comparative agent | 0.1 | 60 |

We claim:

1. A carbamate of the formula $$R^1O-(CH_2)_n \underset{R^2}{\overset{}{\diagdown}} \begin{array}{c} OCON{\diagup}{R^4} \\ {\diagdown}CH_3 \\ N \\ | \\ N-R^3 \\ \| \\ O \end{array}$$ (I)

where either $R^1$ is straight-chain or branched alkyl of not more than 4 carbon atoms and $R^2$ is straight-chain or branched alkyl of not more than 6 carbon atoms, or $R^1$ and $R^2$, together with the molecular moiety which they include, form a 5-membered, 6-membered or 7-membered saturated heterocyclic ring, $R^3$ is straight-chain or branched alkyl of not more than 6 carbon atoms or cycloalkyl of 3 to 6 carbon atoms, $R^4$ is methyl or methoxy, and n is 1 or 2.

2. A carbamate of the formula I as defined in claim 1, where $R^3$ and $R^4$ are each methyl.

3. A carbamate of the formula I as defined in claim 1, wherein $R^1$ and $R^2$, together with the molecular moiety included, form a tetrahydrofuran or tetrahydropyran ring.

4. An isecticidal and acaricidal composition which comprises an effective amount of a carbamate of the formula I as defined in claim 1 and a carrier.

5. A method for combatting insects and acarids, wherein an effective amount of a carbamate of the formula I as defined in claim 1 is allowed to act on the insects or acarids or their habitat.

* * * * *

UNITED STATES PATENT AND TRADEMARK OFFICE
CERTIFICATE OF CORRECTION

PATENT NO. : 4,537,901

DATED : August 27, 1985

INVENTOR(S) : Arno LANGE et al.

It is certified that error appears in the above-identified patent and that said Letters Patent is hereby corrected as shown below:

On the Cover Sheet, please add

[30]  Foreign Application Priority Data

June 15, 1983 [DE] Fed Rep. of Germany ....... 3321519

September 28, 1983 [DE] Fed Rep. of Germany .....3335010

Signed and Sealed this

Twenty-ninth Day of October 1985

[SEAL]

*Attest:*

*Attesting Officer*

DONALD J. QUIGG

*Commissioner of Patents and Trademarks—Designate*